United States Patent [19]
Dellaria et al.

[11] Patent Number: 5,354,865
[45] Date of Patent: Oct. 11, 1994

[54] PHENYLMETHYL DERIVATIVES HAVING LIPOXYGENASE INHIBITORY ACTIVITY

[75] Inventors: Joseph F. Dellaria, Lindenhurst; Linda J. Dorn, Wheeling; Dee W. Brooks, Libertyville, all of Ill.

[73] Assignee: Abbott Laboratories, Abbott Park, Ill.

[21] Appl. No.: 942,870

[22] Filed: Sep. 10, 1992

[51] Int. Cl.⁵ ............... C07D 235/26; C07D 215/227; C07D 265/36
[52] U.S. Cl. ..................... 546/158; 544/105; 548/304.7
[58] Field of Search ........ 546/156, 157, 158; 544/105; 548/304.7; 514/230.5, 312, 387

[56] References Cited

U.S. PATENT DOCUMENTS

| | | | |
|---|---|---|---|
| 5,179,115 | 1/1993 | Bruneau | 514/387 |
| 5,217,969 | 6/1993 | Bruneau | 514/230.5 |
| 5,217,977 | 6/1993 | Crawley | 514/311 |
| 5,217,978 | 6/1993 | Bird | 514/312 |
| 5,240,941 | 8/1993 | Bruneau | 514/312 |
| 5,250,690 | 10/1993 | Turner et al. | 544/354 |

FOREIGN PATENT DOCUMENTS

| | | | |
|---|---|---|---|
| 375404 | 6/1990 | European Pat. Off. | ... C07D 309/10 |
| 385662 | 9/1990 | European Pat. Off. | ... C07D 405/12 |
| 462812 | 12/1991 | European Pat. Off. | ... C07D 409/04 |

*Primary Examiner*—C. Warren Ivy
*Assistant Examiner*—D. Margaret M. Mach
*Attorney, Agent, or Firm*—Jerry F. Janssen

[57] ABSTRACT

Compounds of the structure

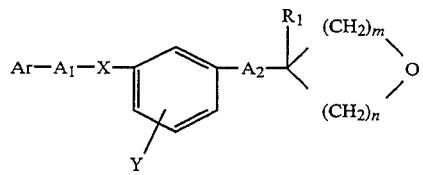

where Ar is optionally substituted carbocyclic aryl, 5- or 6-membered heterocyclic aryl, 10-membered bicyclic heterocyclic aryl containing one or two nitrogen atoms, 9- or 10-membered heterocyclic containing one or two nitrogen atoms and optionally containing a further nitrogen or oxygen atom and one oxo or thioxo substituent, benzo[b]furyl, benzo[b]thienyl, $A_1$ is propynylene, methylene, or a valence bond, X is O, S, $SO_2$, or $NR_2$, Y is selected from alkyl, haloalkyl, alkoxy, halogen, and hydrogen, $A_2$ is selected from

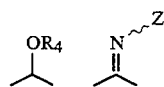

and methylene where Z is $OR_5$ or $NHR_5$ where $R_5$ is hydrogen or alkyl, $R_1$ is hydrogen, alkyl, or $OR_5$, and m and n are integers having a value of 1 or 2 are potent inhibitors of lipoxygenase enzymes and thus inhibit the biosynthesis of leukotrienes. These compounds are useful in the treatment or amelioration of allergic and inflammatory disease states.

7 Claims, No Drawings

PHENYLMETHYL DERIVATIVES HAVING LIPOXYGENASE INHIBITORY ACTIVITY

TECHNICAL FIELD

This invention relates to compounds having biological activity to inhibit lipoxygenase enzymes, to pharmaceutical compositions comprising these compounds, and to a medical method of treatment. More particularly, this invention concerns certain substituted phenylmethyl compounds which inhibit lipoxygenase enzyme activity, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or convened to LTA$_4$. This reactive leukotriene intermediate is enzymatically hydrated to LTB$_4$ or conjugated to the tripeptide glutathione to produce LTC$_4$. LTA$_4$ can also be hydrolyzed nonenzymatically to form two isomers of LTB$_4$. Successive proteolytic cleavage steps convert LTC$_4$ to LTD$_4$ and LTE$_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

SUMMARY OF THE INVENTION

In its principal embodiment, the present invention provides certain substituted phenylmethyl compounds which inhibit lipoxygenase enzyme activity and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

In its principal aspect, the present invention provides compounds having the structure

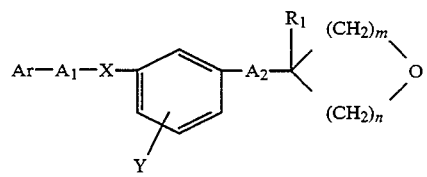

or a pharmaceutically acceptable salt thereof wherein
Ar is selected from the group consisting of
(a) carbocyclic aryl, optionally substituted with alkyl of from one to six carbon atoms, haloalkyl of from one to six carbon atoms, alkoxy of from one to six carbon atoms, or halogen;
(b) 5- or 6-membered heterocyclic aryl, optionally substituted with alkyl of from one to six carbon atoms, haloalkyl of from one to six carbon atoms, alkoxy of from one to six carbon atoms, or halogen;
(c) 10-membered bicyclic heterocyclic aryl containing one or two nitrogen atoms, optionally substituted with alkyl of from one to six carbon atoms, haloalkyl of from one to six carbon atoms, alkoxy of from one to six carbon atoms, or halogen;
(d) benzo[b]furyl, optionally substituted with alkyl of from one to six carbon atoms, haloalkyl of from one to six carbon atoms, alkoxy of from one to six carbon atoms, or halogen;
(e) benzo[b]thienyl, optionally substituted with alkyl of from one to six carbon atoms, haloalkyl of from one to six carbon atoms, alkoxy of from one to six carbon atoms, or halogen;
(f)

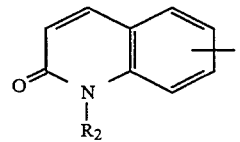

(g)

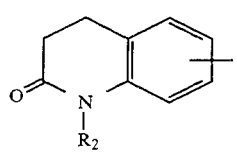

(h)

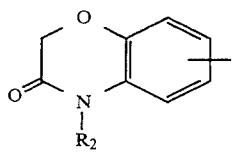

(i)

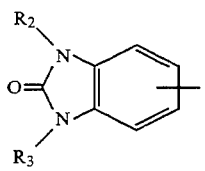

wherein $R_2$ and $R_3$ are independently hydrogen or alkyl of from one to four carbon atoms.

$A_1$ is selected from the group consisting of propynylene, methylene, or a valence bond.

X is selected from the group consisting of O, S, $SO_2$, or $NR_2$, where $R_2$ is as defined above.

Y is selected from the group consisting of alkyl of from one to six carbon atoms, haloalkyl of from one to six carbon atoms, alkoxy of from one to six carbon atoms, halogen, and hydrogen.

$A_2$ is selected from the group consisting of (a)

 (a)

wherein $R_4$ is selected from the group consisting of hydrogen, alkyl of from one to four carbon atoms, alkenyl of from three to six carbon atoms, alkynyl of from three to six carbon atoms, and alkoxyalkyl in which the alkoxy and alkyl groups can independently contain from one to four carbon atoms;

(b)

 (b)

wherein Z is selected from the group consisting of $OR_5$ and $NR_5$, where $R_5$ is selected from the group consisting of hydrogen and alkyl of from one to four carbon atoms, and (c) methylene.

$R_1$ is selected from the group consisting of hydrogen, alkyl of from one to four carbon atoms, and $OR_5$ where $R_5$ is as defined above;

m is 1 or 2; and n is 1 or 2.

In another aspect, the present invention provides pharmaceutical compositions which comprise a therapeutically effective amount of compound as defined above in combination with a pharmaceutically acceptable carrier.

In yet another aspect, the present invention provides a method of inhibiting leukotriene biosynthesis in a host mammal in need of such treatment comprising administering to a mammal in need of such treatment a therapeutically effective mount of a compound as defined above.

DETAILED DESCRIPTION OF THE INVENTION DEFINITIONS OF TERMS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "5- or 6-membered heterocyclic aryl" denotes a monovalent heterocyclic ring group derived by the removal of a single hydrogen atom from a monocyclic heterocyclic ting system obeying the "$4n+2\pi$ electron" or Huckel aromaticity rule. Examples of 5, or 6-membered heterocyclic aryl groups include pyridinyl, furyl, thienyl, thiazolyl, imidazolyl, and pyrimidinyl.

The term "10-membered bicyclic heterocyclic aryl containing one or two nitrogen atoms" refers to a group selected from quinolinyl, isoquinolinyl, quinazolinyl, phthalazinyl, and quinoxalinyl.

The term "9- or 10-membered heterocyclic aryl containing one or two nitrogen and optionally containing a further heteroatom selected from nitrogen or oxygen, and one oxo or thioxo substituent" refers to a group selected from 2-oxo-1,2-dihydroquinolinyl, 2-oxo-1,2,3,4-tetrahydroquinolinyl, 3-oxo-2,3-dihydro-4H-1,4-benzoxazinyl, oxindolinyl, 3-oxo-1,2-dihydro-3H-indazolyl, 2-oxo-2,3-dihydrobenzothiazolyl, 2-oxo-2,3-dihydrobenzimidazolyl, 3-thioxo-2,3-dihydro-4H-1,4-benzoxazinyl, and 2-thioxo-1,2,3,4-tetrahydroquionlinyl.

The term "oxo" denotes a carbonyl oxygen atom.

The term "thioxo" denotes an oxo group as defined above in which the oxygen atom is replaced by a sulfur atom.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynyl" refers to a divalent group derived by the removal of two hydrogen atoms from a straight or branched chain acyclic hydrocarbon group containing a carbon-carbon triple bond.

The term "alkanoyl" represents an alkyl group, as defined above, attached to the parent molecular moiety through a carbonyl group. Alkanoyl groups are exemplified by acetyl, propionyl, butanoyl and the like.

The term "carbocyclic aryl" denotes a monovalent carbocyclic ring group derived by the removal of a single hydrogen atom from a monocyclic or bicyclic fused or non-fused ring system obeying the "4n+2π electron" or Huckel aromaticity rule. Examples of carbocyclic aryl groups include phenyl, 1- and 2-naphthyl, biphenylyl and the like.

The term "metabolically cleavable group" denotes a group which is cleaved in vivo to yield the parent molecule of the structural formulae indicated above wherein M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$-C$_4$ alkyl, halogen, hydroxy or C$_1$-C$_4$ alkoxy. Specific examples of representative metabolically cleavable groups include acetyl, methoxycarbonyl, benzoyl, methoxymethyl and trimethylsilyl groups.

Compounds falling within the scope of the present invention include, but are not limited to:

4-[(3-(naphth-2-yl)methoxyphen-1-yl)hydroxymethyl]tetrahydropyran;

4-[(3-(naphth-2-yl)methoxyphen-1-yl)methoxymethyl]tetrahydropyran;

4-[(3-(naphth-2-yl)methoxyphen-1-yl)ethyloxymethyl]tetrahydropyran;

4-[(3-(naphth-2-yl)methoxyphen-1-yl)allyloxymethyl]tetrahydropyran;

4-[(3-(naphth-2-yl)methoxyphen-1-yl)prop-2-yn-1-yloxymethyl]tetrahydropyran;

4-[(3-(naphth-2-yl)methoxyphen-1-yl)hydrazinomethyl]tetrahydropyran;

E- and Z-O-methyl-4-[(3-((naphth-2-yl)methoxy)phen-1-yl)oximinomethyl]tetrahydropyran;

E- and Z-4-[(3-((naphth-2-yl)methoxy)phen-1-yl)oximinomethyl]tetrahydropyran;

4-[(3-((1,2-dihydro-1-methyl-2-oxoquinolin-6-yl)methoxy)phen-1yl)methoxymethyl]tetrahydropyran;

4-[(3-((1,2-dihydro-1-methyl-2-oxoquinolin-6-yl)methoxy)phen-1-yl)methyloxymethoxymethyl]tetrahydropyran;

E- and Z-4-[(3-((1,2-dihydro-1-methyl-2-oxoquinolin-6-yl)methoxy)phen-1-yl)oximinomethyl]tetrahydropyran;

E- and Z-O-Methyl-4-[(3-((1,2-dihydro-1-methyl-2-oxoquinolin-6-yl)methoxy)phen-1-yl)oximinomethyl]tetrahydropyran;

E- and Z-O-Ethyl-4-[(3-((1,2-dihydro-1-methyl-2-oxoquinolin-6-yl)methoxy)phen-1-yl)oximinomethyl]tetrahydropyran;

4-methoxy-4-[(3-((naphth-2-yl)methoxy)phen-1-yl)methyl]tetrahydropyran;

E- and Z-O-methyl-[(3-((1,2-dihydro-1-methyl-2-oxoquinolin-6-yl)methoxy)-5-fluorophen-1-yl)oximinomethyl]tetrahydropyran;

E- and Z-4-[(3-((1,2-dihydro-1-methyl-2-oxoquinolin-6-yl)methyloxy)-5-fluorophen-1-yl)oximinomethyl]tetrahydropyran;

E- and Z-O-Methyl-3-methyl-3-[(3-((naphth-2-yl)methoxy)-5-fluorophen-1-yl)oximinomethyl]oxetane;

E- and Z-3-methyl-3-[(3 -((naphth-2-yl)methoxy)-5-fluorophen-1-yl)oximinomethyl]oxetane;

E- and Z-3-[(3-((naphth-2-yl)methoxy)-5-fluorophen-1-yl)oximinomethyl]oxetane;

E- and Z-O-methyl-[(3-((naphth-2-yl)methoxy)-5-fluorophen-1-yl)oximinomethyl]oxetane;

E- and Z-3-[(3-((1,2-dihydro-1-methyl-2-oxoquinolin-6-yl)methoxy)-5-fluorophen-1-yl)oximinomethyl]oxetane;

E- and Z-O-methyl-3-[(3-((1,2-dihydro-1-methyl-2-oxoquinolin-6-yl)methoxy)-5-fluorophen-1-yl)oximinomethyl]oxetane;

E and Z-4-[(3-((naphth-2-yl)thioxy)phen-1-yl)oximinomethyl]tetrahydropyran;

E and Z-O-methyl-4-[(3-((naphth-2-yl)thioxy)phen-1-yl)oximinomethyl]tetrahydropyran;

E- and Z-4-[(3-((1,2-dihydro-1-methyl-2-oxoquinolin-6-yl)thioxy)phen-1-yl)oximinomethyl]tetrahydropyran;

E- and Z-O-methyl-4-[(3-((1,2-dihydro-1-methyl-2-oxoquinolin-6-yl)thioxy)phen-1-yl)oximinomethyl]tetrahydropyran;

E- and Z-4-[(3-((naphth-2-yl)thioxy)-5-fluorophen-1-yl)oximinomethyl]tetrahydropyran;

E- and Z-O-methyl-4-[(3-((naphth-2-yl)thioxy)-5-fluorophen-1-yl)oximinomethyl ]tetrahydropyran;

E- and Z-4-[(3-((1,2-dihydro-1-methyl-2-oxoquinolin-6-yl)thioxy)-5-fluorophen-1-yl)oximinomethyl]tetrahydropyran;

E- and Z-O methyl-4-[(3-((1,2-dihydro-1-methyl-2-oxoquinolin-6-yl)thioxy)-5-fluorophen-1-yl)oximinomethyl]tetrahydropyran;

4-[(3-((naphth-2-yl)thioxy)phen-1-yl)methoxymethyl]tetrahydropyran;

4-[(3-((1,2-dihydro-1-methyl-2-oxoquinolin-6-yl)thioxy)phen-1-yl)methoxymethyl]tetrahydropyran;

4-[(3-((naphth-2-yl)thioxy)-5-fluorophen-1-yl)methoxymethyl]tetrahydropyran;

4-[(3-((1,2-dihydro-1-methyl-2-oxoquinolin-6-yl)thioxy)-5-fluorophen-1-yl)methoxymethyl]tetrahydropyran;

E- and Z-O-methyl-4-[(3-((3-(pyridin-2-yl)prop-1-ynyl)methoxy)-5-fluorophen-1-yl)oximino]tetrahydropyran;

E- and Z-O-methyl-4-[(3-((3-(thiazol-2-yl)prop-1-ynyl)methoxy)-5-fluorophen-1-yl)oximino]tetrahydropyran;

4-[(3-((3-(pyridin-2-yl)prop-1-ynyl)methoxy)-5-fluorophen-1-yl)methoxymethyl]tetrahydropyran;

E- and Z-4-[(3-(quionolin-6-yl)methoxyphen-1-yl)oximinomethyl]tetrahydropyran;

E- and Z-4-[(3-(1-methyl-2-oxo-1,2,3,4-tetrahydroquinol-6-yl)methoxyphen-1-yl)oximinomethyl]tetrahydropyran;

E- and Z-4-[(3-(2,2,4-trimethyl-3-oxo-2,3-dihydro-4H-1,4-benzoxazin-7-yl)methoxyphen-1-yl)oximinomethyl]tetrahydropyran;

4-[(3-(quinoxalin-6-yl)methoxyphen-1-yl)methoxymethyl]tetrahydropyran;

4-[(3-(1-methyl-2-oxo-1,2,3,4-tetrahydroquinolin-6-yl)methoxyphen-1-yl)methoxymethyl]tetrahydropyran;

4-[(3-(1,3-dimethyl-2-oxo-2,3-dihydrobenzimidazol-5-yl)methoxyphen-1-yl)methoxymethyl]tetrahydropyran;

Preferred compounds are those in which Ar is selected from the group consisting of naphthyl;

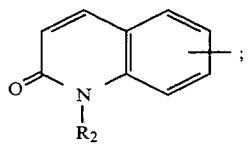

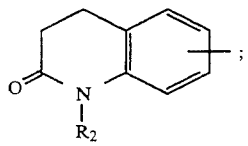

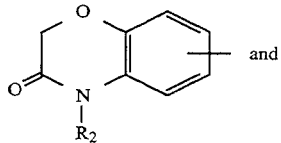 and

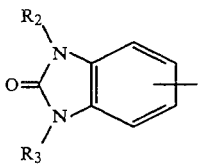

where R2 and R3 are as defined therein.

Particularly preferred compounds of the present invention are:

4-[(3-((naphth-2-yl)methoxy)phen-1-yl)methoxymethyl]tetrahydropyran;

4-[(3-((1,2-dihydro-1-methyl-2-oxoquinolin-6-yl)methoxy)phen-1yl)methoxymethyl]tetrahydropyran;

E- and Z-4-[(3-(1,2-dihydro-1-methyl-2-oxoquinolin-6-yl)methoxyphen-1-yl)oximinomethyl]tetrahydropyran;

E- and Z-O-Methyl-4-[(3-((1,2-dihydro-1-methyl-2-oxoquinolin-6-yl)methoxy)phen-1-yl)oximinomethyl]tetrahydropyran;

E- and Z-O-Ethyl-4-[(3-((1,2-dihydro-1-methyl-2-oxoquinolin-6-yl)methoxy)phen-1-yl)oximinomethyl]tetrahydropyran;

E- and Z-O-methyl-[(3-((1,2-dihydro-1-methyl-2-oxoquinolin-6-yl)methoxy)-5-fluorophen-1-yl)oximinomethyl]tetrahydropyran; and E- and Z-4-[(3-((1,2-dihydro-1-methyl-2-oxoquinolin-6-yl)methyloxy)-5-fluorophen-1-yl) oximinomethyl]tetrahydropyran.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as failing within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 μM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated $LTB_4$ Formation in Human Whole Blood

| Example | $IC_{50}$ ($10^{-6}$ M) |
|---|---|
| 1 | 3.5 |
| 2 | 0.73 |
| 6 | 2.4 |
| 7 | 68% @ 0.39 μM |
| 9 | 0.71 |
| 10 | 0.94 |
| 11 | 73% @ 0.39 μM |
| 12 | 99% @ 0.78 μM |
| 13 | 0.83 |
| 14 | 2.0 |
| 15 | 99.6% @ 0.20 μM |
| 16 | 98% @ 0.78 μM |
| 17 | 2.90 |
| 18 | 5.2 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior m use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating are They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage form for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of This Invention

The compounds of this invention can be prepared by a variety of synthetic routes. Representative procedures are outlined as follows.

Scheme I illustrates a general synthetic route for the preparation of the compounds of this invention which contain an oxime or alkoxy substituent on the group $A_2$. Tetrahydro-4H-pyran-4-carboxylic acid (I) is converted first to the corresponding acid chloride under standard conditions. Treatment with triethylamine and N,O-dimethylhydroxylamine hydrochloride provides the Weinreb amide in excellent overall yield. Differentially protected aryl lithiums are added to obtain the corresponding ketone III. Hydrogenolysis of III or treatment of IIIa with mineral acid provides the free phenol. The phenol is alkylated with naphth-2-ylmethyl chloride to give V. Reduction with $NaBH_4$ in absolute ethanol and subsequent methylation with methyl iodide and sodium hydride provides VII. The naphthyl group can be removed by hydrogenolysis and the phenol alkylated with other electrophiles such as 1,2-dihydro-1-methyl-2-oxo-quinolin-2-ylmethyl bromide to provide VIII. By application of similar alkylation conditions, the phenol IV can be converted to IX and the resulting ketone transformed to the oxime as a mixture of isomers by treatment with the desired O-substituted hydroxylamine hydrochloride in absolute ethanol with pyridine.

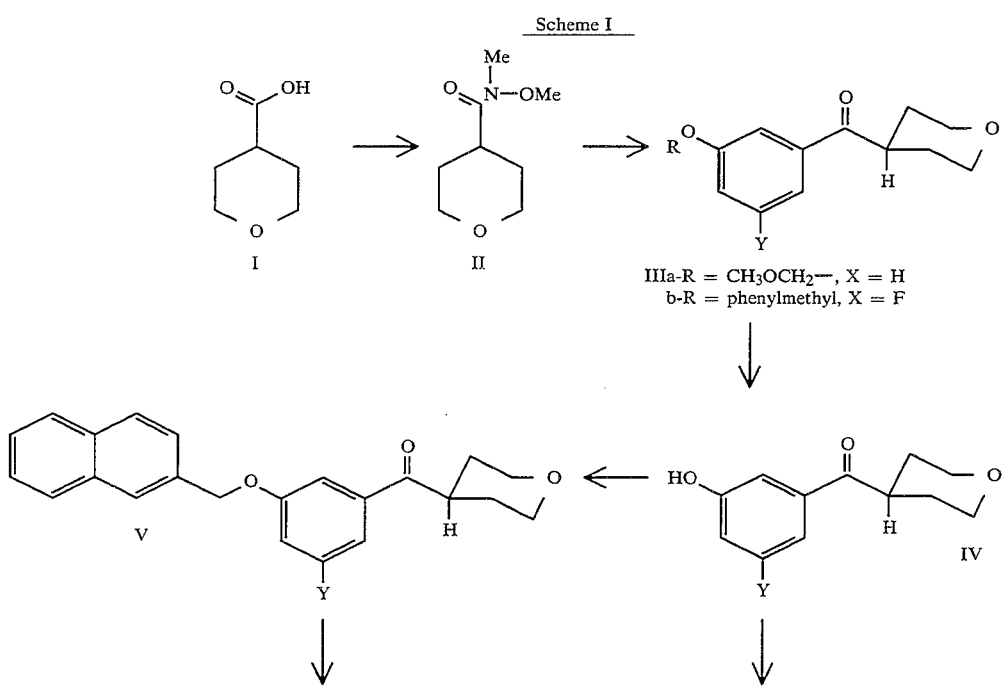

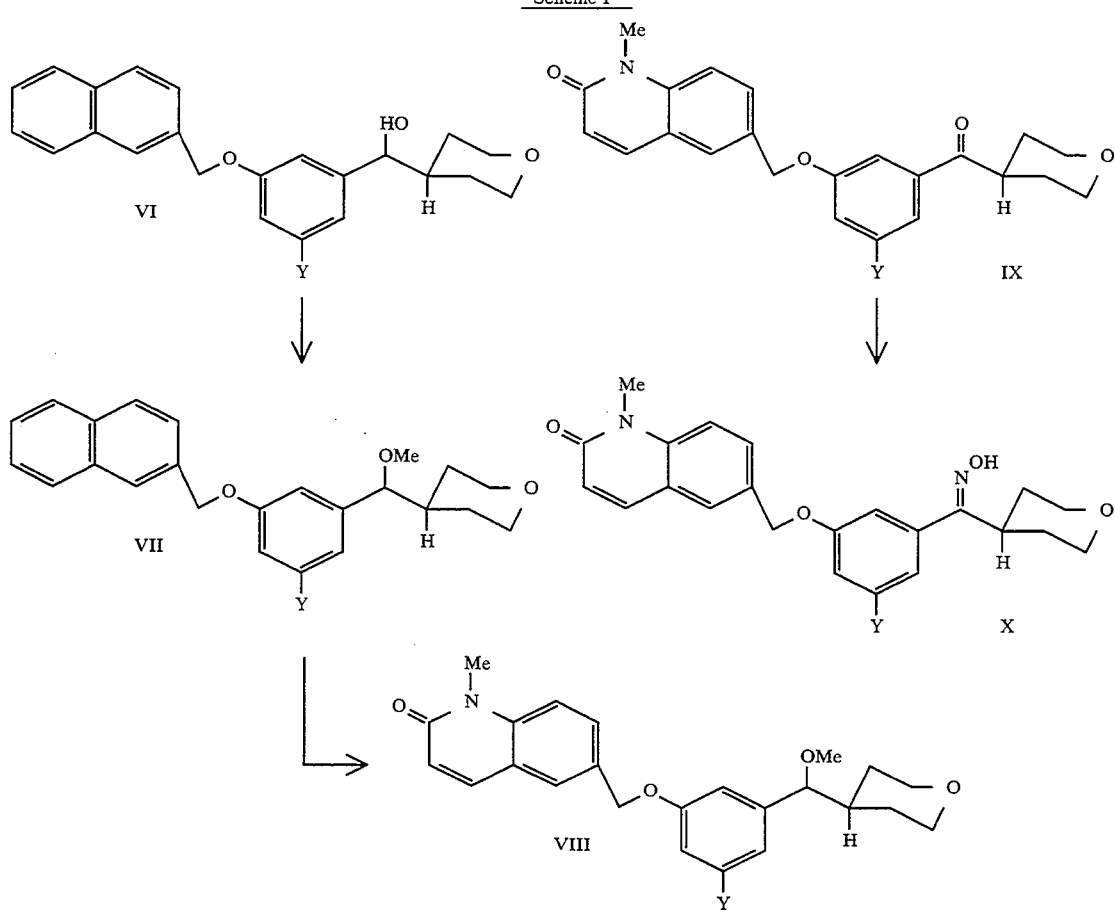

Scheme II illustrates the synthesis of compounds in which the group A2 is methylene. Tetrahydro-4H-pyran-4-one (XI) is converted to the corresponding exoepoxide (XII) (Corey, E. J.; Chaykovsky, M., *Org. Synth.* 49, 78 (1969)). Metallation of 3-methyloxymethylenoxy-bromobezene and addition to epoxide XII provides the tertiary alcohol (XIII). Methylation of the tertiary alcohol, removal of the MOM-protecting group, and alkylation of the phenol were carried out as described in Scheme I.

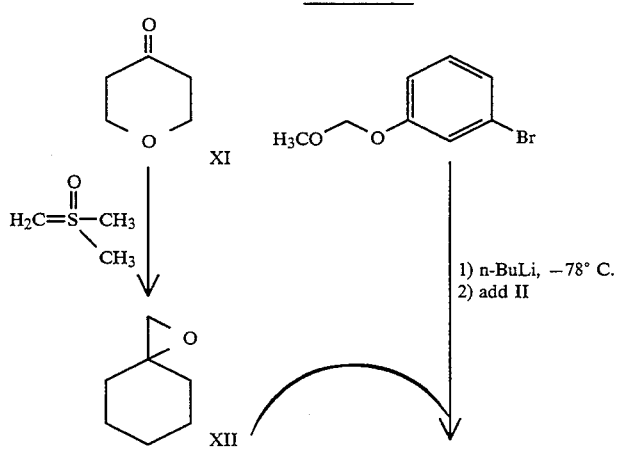

-continued

Scheme II

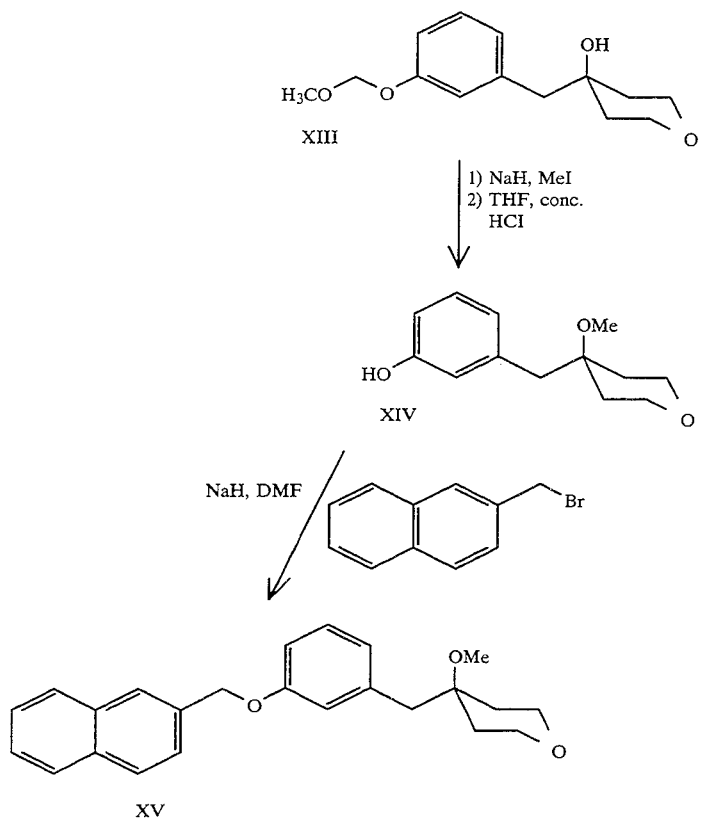

The foregoing may be better understood from the following Examples, which presented for the purpose of illustration and not intended to limit the scope of the inventive concept.

EXAMPLE 1

Preparation of 4-[(3-(naphth-2-yl)methoxyphen-1-yl)hydroxymethyl]-tetrahydropyran.

Step 1. Tetrahydro-4H-pyran-4-(N,O-dimethyl)carboxamide.

A flask was charged with tetrahydro-4H-pyran-4-carboxylic acid (15.3 g, 118 mmol), prepared according to the method of J. v. Braun and Z. Kohler, Chem. Ber., 50, 1657 (1917), dichloromethane (295 mL), and a stir bar. To the resulting solution was added 1 drop of dry dimethylformamide (DMF) and a solution of oxalyl chloride (15.5 mL, 178 mmol) in dichloromethane (47 mL). The reaction was stirred at ambient temperature for one hour and concentrated in vacuo. The resulting slurry was partially dissolved in dichloromethane (20 mL) and concentrated to dryness (2 cycles), then dried briefly under high vacuum. The acid chloride was suspended in dichloromethane (295 mL), cooled to 0° C. and a solution of N,O-dimethylhydroxylamine hydrochloride (12.7 g, 129 mmol) and pyridine (20.9 mL, 259 mmol) in dichloromethane (50 mL) was added. The reaction was quenched by adding excess 10% aqueous hydrochloric acid and stirring for three hours at ambient temperature. After separating the layers, the organic layer was washed with saturated aqueous HaHCO3 and brine, dried over MgSO4, filtered, and concentrated in vacuo to provide the corresponding amide as an orange liquid (18.9 g, 92%).

Step 2. 3-methyloxymethoxy-bromobenzene.

To a solution of 3-bromophenol (27.4 g, 158 mmol) in CH2Cl2 was added chloromethyl methyl ether (18 mL, 237 mmol). The reaction mixture was cooled to 0° C. and diisopropylethylamine (55 mL, 316 mmol) was added and the cold bath was removed. The reaction mixture was stirred for 3 hours at ambient temperature and then poured into 10% aqueous HCl. The layers were separated and the aqueous phase was extracted 4 times with CH2Cl2. The combined organic layers were washed once each with saturated aqueous NaHCO3, 15% aqueous NaOH, and brine, dried over MgSO4, filtered, and concentrated in vacuo to provide 3-methyloxymethoxy-bromobenzene as a yellow oil.

Step 3. 4-[3-(methyloxymethoxyphen-1-yl)oxomethyl]-tetrahydropyran.

An oven-dried flask was charged with 3-methoxymethoxy-bromobenzene (2.29 g, 10.62 mmol), prepared as in step 2, freshly dried THF (43 mL), and a stir bar. The flask was fitted with a septum, a nitrogen inlet, and a nitrogen outlet before cooling to −78° C. under a flow of nitrogen. To the cooled reaction mixture was added n-butyl lithium (4.24 mL, 2.5M, 10.62 mmol in hexanes). The resulting solution was stirred at −78° C. for 0.5 hours after which a solution of tetrahydro-4H-pyran-4-(N,O-dimethyl)carboxamide (1.7 g, 10.62 mmol), prepared as in step 1, in THF (10 mL) was added. The reaction mixture was stirred 0.5 hours at −78° C., 0.5 hours at ambient temperature, and then quenched with water. The reaction mixture was partitioned between water and ethyl acetate. The organic layer was washed with saturated ammonium chloride and brine, dried over MgSO₄, filtered and concentrated in vacuo to provide a yellow oil. Pure 4-[3-(methoxymethoxyphen-1-yl)oxomethyl]tetrahydropyran (1.5 g, 57%) was obtained by chromatography on silica gel (30% ethyl acetate/hexanes).

Step 4. 4-[3-(hydroxyphen-1-yl)oxomethyl]tetrahydropyran.

The methyloxymethoxy group was removed by treatment of 4-[3-(methyloxymethoxyphen-1-yl)oxomethyl]tetrahydropyran (0.82 g, 3.27 mmol), prepared as in step 3 with concentrated hydrochloric acid (2.45 mL, 0.75 mL/mmol) in THF (13 mL) at ambient temperature for 0.5 hours. The reaction mixture was partitioned between water and ethyl acetate and the aqueous layer was extracted twice with ethyl acetate. The combined organic layers were washed with saturated aqueous sodium bicarbonate and brine, dried over MgSO₄, filtered, and concentrated in vacuo to provide 4-[3-(hydroxyphen-1-yl)oxomethyl]tetrahydropyran as a brown solid (0.65 g, 96%) which was used without further purification.

Step 5. 4-[(3-(naphth-2-yl)methoxyphen-1-yl)oxomethyl]tetrahydropyran.

An oven-dried flask was charged with sodium hydride (0.36 g, 80% dispersion, 11.9 mmol), THF (110 mL), and a stir bar. A solution of 4-[3-(hydroxyphen-1-yl)oxomethyl]tetrahydropyran (2.05 g, 9.95 mmol), prepared as in step 4, in dry DMF (15 mL), was added to the stirred reaction mixture under a stream of nitrogen. After gas evolution ceased 2-bromomethylnaphthalene (2.2 g, 9.95 mmol) was added and the resulting mixture was stirred for one hour at ambient temperature. The reaction was quenched with water and partitioned between water and ethyl acetate. The organic layer was washed with saturated aqueous sodium bicarbonate and brine, dried over MgSO₄, filtered, and concentrated in vacuo to provide a yellow oil. Pure 4-[3-((naphth-2-yl)methoxyphen-1-yl)oxomethyl]tetrahydropyran (3.0 g, 87%) was obtained by chromatography on silica gel (30% ethyl acetate/hexanes) as a colorless solid (top 101°–102° C.).

Step 6. 4-[(3-(naphth-2-yl)methoxyphen-1-yl)hydroxymethyl]tetrahydropyran.

4-[(3-(naphth-2-yl)methoxyphen-1-yl)oxomethyl]tetrahydropyran (200 mg, 0.58 mmol) prepared as in step 5, was treated with NaBH₄ (21.8 mg, 0.58 mmol) in absolute ethanol (5 mL) at ambient temperature for 4 hours. The reaction was partitioned between water and ethyl acetate: The organic layer was washed with saturated aqueous sodium bicarbonate and brine, dried over MgSO₄, filtered, and concentrated in vacuo to provide a yellow solid. 4-[(3-(naphth-2-yl)methoxyphen-1-yl)hydroxymethyl]tetrahydropyran (3.0 g, 87%), was obtained by chromatography on silica gel (30% ethyl acetate/hexanes) as a colorless solid. Recrystallization from ethyl acetate provided an analytically pure sample. mp 120°–121° C. $^1$H NMR (300 MHz, CDCl₃) δ7.80–7.90 (4H, m), 7.45–7.55 (3H, m), 7.27 (1H, t, J=7 Hz), 6.86–6.98 (3H, m), 5.24 (2H, s), 4.33 (1H, d, J=7 Hz), 3.97 (1H, dd, J=12, 4.5 Hz), 3.82 (1H, dd, J=12, 4 Hz), 3.33 (1H, dt, J=12, 12, 1.5 Hz), 3.19 (1H, dt, J=12, 12, 2 Hz), 1.73–1.89 (2H, m), 1.22–1.50 (2H, m), 1.11 (1H, br d, J=12 Hz). MS 366 (M+NH₄)⁺, 348 (M+H)⁺. Analysis calc'd for C₂₃H₂₄O₃: C, 79.38; H, 6.94. Found: C, 79.10; H, 6.83.

EXAMPLE 2

Preparation of 4-[(3-(naphth-2-yl)methoxyphen-1-yl)methoxymethyl]tetrahydropyran.

4-[(3-(naphth-2-yl)methoxyphenyl)hydroxymethyl]tetrahydropyran (160 mg, 0.46 mmol), prepared according to the method of Example 1, was added slowly to a suspension of sodium hydride (27.5 mg, 0.92 mmol, 80% oil dispersion) in dry THF under a stream of nitrogen. When the gas evolution ceased, methyl iodide (77 µL, 1.23 mmol) was added neat, and the reaction mixture was stirred at ambient temperature for five hours. The reaction was quenched with water and partitioned between water and ethyl acetate. The organic layer was washed with brine, dried over MgSO₄, filtered and concentrated in vacuo to provide a yellow oil. Purification by chromatography on silica gel (30% ethyl acetate/hexanes) provided 4-[(3-(naphth-2-yl)methoxyphen-1-yl)methoxymethyl]tetrahydropyran (100 mg, 60%). $^1$H NMR (300 MHz, CDCl₃) δ7.80–7.90 (4H, m), 7.45–7.55 (3H, m), 7.27 (1H, t, J=7 Hz), 6.90–6.98 (2H, m), 6.83 (1H, d, J=7.5 Hz), 5.25 (2H, s), 3.94 (1H, br dd, J=12, 4.5 Hz), 3.78 (1H, br dd, J=12, 4 Hz), 3.73 (1H, d, J=7.5 Hz), 3.29 (1H, dt, J=12, 12, 1.5 Hz), 3.18 (3H, s), 3.16 (1H, dt, J=12, 12, 2 Hz), 1.88 (1H, br d, J=13.5 Hz), ca 1.75 (1H, 11 lined multiplet), 1.38 (1H, dq, J=4.5, 12, 12 Hz), 1.23 (1H, dq, J=4.5, 12, 12 Hz), 1.03 (1H, br d, J=12 Hz). MS 380 (M+NH₄), 362 (M+H)⁺. Analysis calc'd for C₂₄H₂₆O₃: C, 79.52; H, 7.23. Found: C, 79.24; H, 7.16.

EXAMPLE 3

Preparation of 4-[(3-(naphth-2-yl)methoxyphen-1-yl)ethyloxymethyl]tetrahydropyran.

The desired compound is prepared according to the method of Example 2, except substituting ethyl iodide for methyl iodide.

EXAMPLE 4

Preparation of 4-[(3-(naphth-2-yl)methoxyphen-1-yl)allyloxymethyl]tetrahydropyran.

The desired compound is prepared according to the method of Example 2, except substituting allyl iodide for methyl iodide.

EXAMPLE 5

Preparation of 4-[(3-(naphth-2-yl)methoxyphen-1-yl)prop-2-yn-1-yloxymethyl]tetrahydropyran.

The desired compound is prepared according to the method of Example 2, except substituting propargyl bromide for methyl iodide.

EXAMPLE 6

Preparation of 4-[(3-(naphth-2-yl)methoxyphen-1-yl)hydrazinomethyl]tetrahydropyran.

The desired compound was prepared by treatment of 4-[(3-(naphth-2yl)methoxyphenyl]oxomethyl]tetrahydropyran (50 mg, 0.144 mmol), prepared as in Example 1, steps 1–5, with hydrazine monohydrate (8 µL, 0.173 mmol) and catalytic acetic acid (2 drops) in ethanol (6 mL) at reflux for 2 hours. The reaction was concentrated in vacuo and recrystallized from ethyl acetate to provide the title compound as a colorless solid (50 mg, 95%). mp 145°–147° C. $^1$H NMR (300 MHz, CDCl$_3$) δ7.80–7.90 (4H, m), 7.45–7.55 (3H, m), 7.38 (1H, t, J=7 Hz), 7.05 (1H, ddd, J=9, 2.5, 0.75 Hz), 6.80 (1H, br s), 6.76 (1H, br d, J=7.5 Hz), 5.27 (2H, s), 3.91 (2H, dt, J=12, 3, 3 Hz), 3.33 (2H, m), 2.58 (1H, m), 1.57–1.67 (4H, m). MS 361 (M+H)$^+$. Analysis calc'd for C$_{23}$H$_{24}$N$_2$O$_2$(0.5 H$_2$O): C, 74.77; H, 6.82; N, 7.58. Found: C, 74.42; H, 6.50; N, 7.31.

EXAMPLE 7

Preparation of E- and Z-O-methyl-4-[(3-(naphth-2-yl)methoxyphen-1-yl)oximinomethyl]tetrahydropyran.

The desired compound was prepared by treatment of 4-[(3-(naphth-2-yl)methoxyphen-1-yl)oxomethyl]tetrahydropyran (50 mg, 0.144 mmol), prepared as in Example 1, steps 1–5, with O-methylhydroxylamine hydrochloride (14.5 mg, 0.173 mmol), catalytic pyridine (2 drops), and acetic acid (2 drops) in ethanol (6 mL) at reflux for 0.5 hours. The reaction was concentrated in vacuo and partitioned between ethyl acetate and water. The organic layer was washed with saturated aqueous sodium bicarbonate and brine, dried over MgSO$_4$, filtered and concentrated in vacuo to provide a colorless solid. Chromatography on silica gel (20% ethyl acetate/hexanes) provided the title compounds (38 mg, 70%) as a colorless solid in a 1:1 ratio of the E:Z isomers. mp 82°–85° C. $^1$H NMR (300 MHz, CDCl$_3$) δ7.80–7.90 (4H, m), 7.45–7.55 (3H, m), 7.25–7.34 (1H, m), 6.95–7.03 (2H, m), 6.84 (1H/2, br s), 6.80 (1H/2, br d, J=7.5 Hz), 5.26 and 5.24 (2H/2, s), 3.94 (3H/2, s), 3.88–3.94 (2H, m), 3.43 (2H/2, dt, J=12, 2 Hz), 3.29–3.45 (1H, m), 2.62 (1H/2, ddd, J=12, 6, 3 Hz), 1.84 (1H, dq, J=12, 12, 12, 4.5 Hz), 1.58–1.68 (3H, m). MS 376 (M+H)$^+$. Analysis calc'd for C$_{24}$H$_{25}$NO$_3$: C, 76.77; H, 6.71; N, 3.73. Found: C, 76.65; H, 6.59; N, 3.57.

EXAMPLE 8

Preparation of E- and Z-4-[(3-(naphth-2-yl)methoxyphen-1-yl)oximinomethyl]tetrohydropyran.

The title compounds were prepared according to the method of Example 7 except substituting hydroxylamine hydrochloride for O-methylhydroxylamine hydrochloride to provide a mixture of the title compounds as a colorless solid. The pure geometric isomers were separated by silica gel chromatography.

E-isomer. mp 152°–154° C. $^1$H NMR (300 MHz, acetone-D$_6$) δ10.18 (1H, s), 8.01 (1H, br s), 7.88–7.97 (3H, m), 7.63 (1H, dd, J=9, 2 Hz), 7.47–7.57 (2H, m), 7.27–7.34 (1H, 6-lined m), 7.05–7.11 (2H, m), 7.00 (1H, dt, J=7.5, 1,1 Hz), 5.34 (2H, s), 3.86 (2H, dd, J=12, 4.5 Hz), 3.52 (1H, tt, J=12, 4.5 Hz), 3.39 (2H, dt, J=3, 12, 12 Hz), 1.83–2.00 (2H, m), 1.58 (2H, br d, J=12 Hz). MS 362 (M+H)$^+$, 379 (M+NH$_4$)$^+$. Analysis calc'd for C$_{23}$H$_{23}$NO$_3$(0.20 H$_2$O): C, 75.68; H, 6.46; N, 3.84. Found: C, 75.74; H, 6.09; N, 4.16.

Z-isomer: mp 149°–151° C. $^1$H NMR (300 MHz, acetone-D$_6$) δ9.67 (1H, s), 8.01 (1H, br s), 7.88–7.97 (3H, m), 7.63 (1H, dd, J=9, 2 Hz), 7.47–7.57 (2H, m), 7.33 (1H, t, J=8 Hz), 7.00–7.09 (2H, m), 6.91 (1H, dt, J=7.5, 1, 1 Hz), 5.33 (2H, s), 3.83 (2H, ddd, J=12, 4.5, 3.0 Hz), 3.29 (1H, dt, J=3, 12, 12 Hz), 2.71 (1H, tt, J=4.5, 12 Hz), 1.46–1.68 (4lt, m). MS 362 (M+H)$^+$, 379 (M+NH$_4$)$^+$. Analysis calc'd for C$_{23}$H$_{23}$NO$_3$(0.20 H$_2$O): C, 75.68; H, 6.46; N, 3.84. Found: C, 75.74; H, 6.09; N, 4.16.

EXAMPLE 9

Preparation of 4-[(3-(1,2-dihydro-1-methyl-2-oxoquinolin-6-yl)methyloxyphen-1-yl)methoxymethyl]tetrahydropyran.

Step 1. 4-[(3-(1,2-dihydro-1-methyl-2-oxoquinolin-6-yl)methoxyphen-1yl)oxomethyl]tetrahydropyran.

The desired compound was prepared according to the method of Example 1, step 5, except substituting 1,2-dihydro-1-methyl-2-oxoquinolin-6-yl-methyl bromide, prepared as described in EPA 385–679, for 2-bromomethylnaphthalene.

Step 2. Preparation of 4-[(3-(1,2-dihydro1-methyl-2-oxoquinolin-6-yl)methyloxyphen-1-yl)methoxymethyl]tetrahydropyran.

The desired compound was prepared according to the method of Example 2, except substituting 4-[(3-(1,2-dihydro-1-methyl-2-oxoquinolin-6-yl)methyloxyphen-1-yl)oxomethyl]tetrahydropyran, prepared as in step 1, for 4-[(3-(naphth-2-yl)methoxyphen-1-yl)oxomethyl]tetrahydropyran. $^1$H NMR (300 MHz, CDCl$_3$) δ7.62–7.73 (3H, m), 7.40 (1H, d, J=9 Hz), 7.24–7.33 (1H, m), 6.89–6.94 (2H, m), 6.86 (1H, d, J=7.5 Hz), 6.73 (1H, d, J=9 Hz), 5.13 (2H, s), 3.97 (1H, br dd, J=12, 4.5 Hz), 3.84 (1H, br dd, J=12, 4.5 Hz), 3.76 (1H, d, J=8 Hz), 3.73 (3H, s), 3.33 (1H, dt, J=12, 12, 2.5 Hz), 3.23 (1H, dt, J=12, 12, 4.5 Hz), 1.93 (1H, br d, J=13 Hz), 1.78 (1H, 11 lined m), 1.20–1.48 (3H, m), 1.11 (1H, br d, J=12 Hz); MS 411 (M+NH$_4$), 394 (M+H)$^+$. Analysis calc'd for C$_{24}$H$_{27}$NO$_4$: C, 73.26; H, 6.91; N, 3.55. Found: C, 72.50; H, 6.78; N, 3.52.

EXAMPLE 10

Preparation of 4-[(3-((1,2-dihydro-1-methyl-2-oxoquinolin-6-yl)methoxy)-phen-1-yl)methoxymethoxymethyl]tetrahydropyran.

The desired compound was prepared according to the method of Example 2, except substituting 4-[(3-(1,2-dihydro-1-methyl-2-oxoquinolin-6-yl)methyloxyphen-1-yl)oxomethyl]tetrahydropyran, prepared as in Example 9 step 1, for 4-[(3-(naphth-2-yl)methoxyphen-1-yl)oxomethyl]tetrahydropyran, and substituting chloromethyl methyl ether for methyl iodide. $^1$H NMR (300 MHz, CDCl$_3$) δ7.62–7.70 (3H, m), 7.39 (1H, d, J=9 Hz), 7.24–7.30 (1H, m), 6.87–6.94 (3H, m), 6.73 (1H, d, J=9 Hz), 5.13 (2H, s),4.52 (1H,AB, J=6 Hz), 4.47 (1H,AB, J=6 Hz), 4.27 (1H, d, J=8.5 Hz), 4.01 (1H, br dd, J=12, 4.5 Hz), 3.87 (1H, br dd, J=12, 4.5 Hz), 3.74 (3H, s), 3.38 (3H, s), 3.37 (1H, dt, J=12, 12, 2.5 Hz), 3.26 (1H, dt, J=12, 12, 4.5 Hz), 1.93 (1H, br d, J=13 Hz), 1.76 (1H, 11 lined m), 1.46 (1H, dq, J=13, 13, 13 4.5 Hz), 1.32 (1H, dq, J=13, 13, 13, 4.5 Hz), 1.11 (1H, br d, J=12 Hz). MS 441 (M+NH$_4$), 424 (M+H)$^+$. Analysis calc'd for C$_{25}$H$_{29}$NO$_5$(0.6 H$_2$O): C, 69.14; H, 7.01; N, 3.22. Found: C, 68.90; H, 6.52; N, 3.11.

EXAMPLE 11

Preparation of E- and Z-4-[(3-((1,2-dihydro-1-methyl-2-oxoquinolin-6-yl)methoxy)phen-1-yl)oximinomethyl]tetrahydropyran.

A 1:1 ratio of E and Z isomers was obtained according to the method of Example 8, except substituting 4-[(3-(1,2-dihydro-1-methyl-2-oxoquinolin-6-yl)methyloxyphen-1-yl)oxomethyl]tetrahydropyran, prepared as in Example 9 step 1, for 4-[(3-(naphth-2-yl)methoxyphen-1-yl)oxomethyltetrahydropyran. Partial separation was achieved by chromatography over silica gel using 80% ethyl acetate/carbon tetrachloride as the eluant and combining pure fractions early and late in the elution of the product. The more mobile spot was assigned as the E-isomer and the more polar spot was assigned as the Z-isomer.

E-isomer (Example 11a). mp 148°–149° C. $^1$H NMR (300 MHz, CDCl$_3$) $\delta$7.60–7.72 (3H, m), 7.45–7.55 (3H, m), 7.39 (1H, d, J=9 Hz), 7.25–7.33 (1H, m), 7.00 (1H, AB, J=4 Hz), 6.97 (1H, AB, J=4 Hz), 6.73 (1H, d, J=9.5 Hz), 5.14 (2H, s), 3.98 (2H, br dd, J=13, 4.5 Hz), 3.73 (3H, s), 3.55 (1H, tt, J=13, 13, 4.5, 4.5 Hz), 3.48 (2H, dt, J=2, 13, 13 Hz), 1.89 (2H, dq, J=4.5, 13, 13, 13 Hz), 1.67 (2H, br d, J=13 Hz). MS 393 (M+H)$^+$. Analysis calc'd for C$_{23}$H$_{24}$N$_2$O$_4$: C, 70.39; H, 6.16; N, 7.14. Found: C, 70.25; H, 5.98; N, 6.95.

Z-isomer (Example 11b). mp 184°–185° C. $^1$H NMR (300 MHz, CDCl$_3$) $\delta$7.60–7.72 (3H, m), 7.25–7.53 (3H, m), 6.85–7.03 (3H, m), 6.73 (1H, d, J=9.5 Hz), 5.14 (2H, s), 3.98 (2H, br m), 3.73 (3H, s), 3.37–3.60 (2H, m), 2.70 (1H, m), 1.89 (2H, dq, J=4.5, 13, 13, 13 Hz), 1.68 (2H, br m). MS 393 (M+H)$^+$. Analysis calc'd for C$_{23}$H$_{24}$N$_2$O$_4$: C, 70.39; H, 6.16; N, 7.14. Found: C, 70.25; H, 5.98; N, 6.95.

EXAMPLE 12

Preparation of E- and Z-O-Methyl-4-[(3-((1,2-dihydro-1-methyl-2-oxoquinolin-6-yl)methoxy)-phen-1-yl)oximinomethyl]tetrahydropyran.

The desired compound was prepared according to the method of Example 7, except substituting 4-[(3-(1,2-dihydro-1-methyl-2-oxoquinolin-6-yl)methoxyphen-1yl)oxomethyl]tetrahydropyran, prepared as in Example 9 step 1, for 4-[(3-(naphth-2-yl)methoxyphen-1-yl]4-oxomethyltetrahydropyran. Purification by silica gel chromatography yielded the title compounds as a colorless oil in a 1:1 ratio of the E:Z isomers (58 mg, 54%). $^1$H NMR (300 MHz, CDCl$_3$) $\delta$7.60–7.72 (3H, m), 7.25–7.42 (2H, m), 6.80–7.00 (3H, m), 6.73 (1H, d, J=9.5 Hz), 5.14 and 5.12 (2H, 2s), 3.94–3.98 (2H, m), 3.93 (1.5H, s), 3.70 (1.5H, s), 3.34–3.50 (2.5H, m), 2.68 (0.5H, br pentet, J=8 Hz), 1.89 (1H, dq, J=4.5, 13, 13, 13 Hz), 1.60–1.72 (3H, m). MS 407 (M+H)$^+$. Analysis calc'd for C$_{24}$H$_{26}$N$_2$O$_4$: C, 70.92; H, 6.45; N, 6.89. Found: C, 70.83; H, 6.48; N, 6.80.

EXAMPLE 13

Preparation of E- and Z-O-Ethyl-4-[(3-((1,2-dihydro-1-methyl-2-oxoquinolin-6-yl)methoxy)phen-1-yl)oximinomethyl]tetrahydropyran.

The desired compound was prepared according to the method of Example 7, except substituting 4-[(3-(1,2-dihydro-1-methyl-2-oxoquinolin-6-yl)methoxyphen-1-yl)oxomethyl]tetrahydropyran, prepared as in Example 9 step 1, for 4-[(3-(naphth-2-yl)methoxyphen-1-yl)oxomethyl]tetrahydropyran, and substituting O-ethylhydroxylamine hydrochloride for O-methyl-hydroxylamine hydrochloride. Purification by silica gel chromatography (5% methanol/ethyl acetate) yielded the title compounds as a colorless oil in a 1:1 ratio of the E:Z isomers (87 mg, 77%). $^1$H NMR (300 MHz, CDCl$_3$) $\delta$7.60–7.72 (3H, m), 7.25–7.42 (2H, m), 6.80–7.00 (3H, m), 6.73 (1H, d, J=9.5 Hz), 5.14 and 5.12 (2H total, 2s), 4.19 and 4.06 (2H total, 2q, J=7 Hz), 3.74 (3H, s), 3.35–3.51 (2.5H, m), 2.68 (0.5H, br pentet, J=8 Hz), 1.90 (1H, dq, J=4.5, 13, 13, 13 Hz), 1.60–1.72 (3H, m), 1.31 and 1.19 (3H total, 2t, J=7 Hz). MS 421 (M+H)$^+$. Analysis calc'd for C$_{25}$H$_{28}$N$_2$O$_4$: C, 71.41; H, 6.71; N, 6.66. Found: C, 71.29; H, 6.74; N, 6.78.

EXAMPLE 14

Preparation of 4-methoxy-4-[(3-((naphth-2-yl)methoxy)phen-1-yl)methyl]tetrahydropyran.

Step 1. spiro[oxirane-1,4'-4'H-tetrahydropyran].

Tetrahydro-4H-pyran-4-one (5.0 g, 49.9 mmol) was reacted with the sodium anion of trimethylsulfoxonium iodide (12.6 g, 57.4 mmol) according to the procedure of Corey, E. J, and Chaykovsky, M, Org. Synth., 49, 78, (1969) to provide the corresponding exo-epoxide as a liquid. Distillation (bp 61°–62° C.) provided the pure epoxide (3.6 g, 58%).

Step 2. 4-hydroxy-4-[(3-(methyloxymethoxy)phen-1-yl)methyl]tetrahydropyran.

3-methyloxymethoxy-bromobenzene (928 mg, 4.3 mmol) was treated with n-butyllithium (2.5M solution in hexanes, 1.7 mL, 4.3 mmol) at −78° C. as described in Example 1, step 3. The −78° C. lithium anion solution was transferred to a −78° C. solution of BF$_3$Et$_2$O (0.559 mL, 4.3 mmol) in freshly dried THF (30 mL). A solution of spiro[oxirane-1,4'-4'H-tetrahydropyran] (0.5 g, 4.3 mmol), prepared as in step 1, in THF (3 mL) was added to the anion solution and the resulting solution was stirred 1.5 hours at −78° C. and then overnight at −10° C. under a nitrogen atmosphere. The reaction was quenched by the addition of excess saturated aqueous sodium bicarbonate. The volatiles were removed in vacuo and the resulting aqueous solution was extracted with ether (5×, 30 mL). The combined organic layers were washed twice with brine, dried over MgSO$_4$, filtered, and concentrated in vacuo to provide a cloudy oil. Purification by chromatography on silica gel (35 g, 20% ethyl acetate/hexanes) provided 4-hydroxy-4-[(3-(methyloxymethoxy)phen-1-yl)methyl]tetrahydropyran (326 mg, 30%).

Step 3. 4-methoxy-4-[(3-(methyloxymethoxy)phen-1-yl)methyl]tetrahydropyran.

The desired compound was prepared according to the method of Example 2, except substituting 4-hydroxy-4-[(3-(methyloxymethoxyphen-1-yl)methyl]-tetrahydropyran (295 mg, 1.18 mmol), prepared as in step 2, for 4-[(3-(naphth-2-yl)methoxyphen-1-yl)hydroxymethyl]tetrahydropyran. Chromatography on silica gel (30% ethyl acetate/hexanes) provided 4-methoxy-4-[(3-(methyloxymethoxy)phen-1-yl)methyl]-tetrahydropyran (156 mg, 50%).

Step 4. 4-methoxy-4-[(3-hydroxyphen-1-yl)methyl]tetrahydropyran.

The desired compound was prepared according to the method of Example 1, step 4, except substituting 4-methoxy-4-[(3-(methyloxymethoxyphen-1-yl)methyl]tetrahydropyran (150 mg, 0.568 mmol) for 4-[3-(methyloxymethoxyphen-1-yl)oxomethyl]tetrahydropyran. 4-methoxy-4-[(3-hydroxyphen-1yl)methyl]tetrahydropyran (40 mg, 32%) was obtained by silica gel chromatography using 50% ethyl acetate/hexanes as the eluant.

Step 5. 4-methoxy-4-[(3-(naphth-2-yl)methoxyphen-1-yl)methyl]tetrahydropyran.

The desired compound was prepared according to the method of Example 1, step 5 except substituting 4-methoxy-4-[(3-hydroxyphen-1-yl)methyl]tetrahydropyran (150 mg, 0.568 mmol), prepared as in step 4, for 4-[3-(hydroxyphen-1-yl)oxomethyl]tetrahydropyran. Silica gel chromatography using 30% ethyl acetate/hexanes as the eluant provided 4-methoxy-4-[(3-(naphth-2-yl)methoxyphen-1-yl)methyl]tetrahydropyran (39 mg, 59%). $^1$H NMR (300 MHz, CDCl$_3$) δ7.80–7.90 (4H, m), 7.45–7.55 (3H, m), 7.27 (1H, t, J=7 Hz), 6.88 (1H, dd, J=7.5, 3 Hz), 6.73–6.82 (2H, d, m), 5.22 (2H, s), 3.62 (4H, br dd, J=4.5, 6.5 Hz), 3.29 (3H, s), 2.73 (2H, s), 1.54 (4H, br dd, J=4.5, 6.5 Hz). MS 380 (M+NH$_4$)$^+$. Analysis calc'd for C$_{24}$H$_{26}$O$_3$: C, 79.53; H, 7.23. Found: C, 79.39; H, 6.96.

EXAMPLE 15

Preparation of E- and Z-O-methyl-[(3-((1,2-dihydro-1-methyl-2-oxoquinolin-6-yl)methoxy)-5-fluorophen-1-yl)oximinomethyl]tetrahydropyran.

Step 1. 3-benzyloxy-5-fluorobromobenzene.

Sodium hydride (80% oil dispersion, 6.0 g, 201 mmol) was added slowly to a solution of benzyl alcohol (16 mL, 155 mmol) in THF (310 mL) at 0° C. DMF (300 mL) was added slowly and the reaction mixture was stirred until all of the NaH dissolved and gas evolution ceased. A solution of 1-bromo-3,5-difluorobenzene (30 g, 155 mmol) in THF (30 mL) was added and the reaction mixture was stirred for 30 min at ambient temperature. The reaction was quenched with saturated aqueous NH$_4$Cl, and the reaction mixture was extracted 3 times with ethyl acetate. The combined organic layers were washed with saturated aqueous NH$_4$Cl and brine, dried over MgSO$_4$, filtered, and concentrated in vacuo to give a yellow liquid. 3-benzyloxy-5-fluorobromobenzene (28 g) was isolated by chromatography on silica gel (5% ethyl acetate, hexanes). Step 2. 4-[(3-benzyloxy-5-fluorophen-1-yl)oxomethyl]tetrahydropyran.

The desired compound was prepared according to the method of Example 1, step 3 except substituting 3-benzyloxy-5-fluorobromobenzene for 3-methoxymethoxy-bromobenzene.
Step 3. 4-[(3-hydroxy-5-fluorophen-1-yl)oxomethyl]tetrahydropyran.

To a suspension of palladium on carbon (1.5 g) in ethanol (30 mL) under N$_2$ was added a solution of 4-[(3-benzyloxy-5-fluorophen-1-yl)oxomethyl]tetrahydropyran (3.7 g, 12 mmol) in ethanol (70 mL). The reaction mixture was flushed three times with hydrogen, was then stirred for three hours under positive hydrogen pressure. The reaction mixture was flushed with N$_2$, faltered through a pad of celite, and concentrated in vacuo to yield 4-[(3-hydroxy-5-fluorophen-1-yl)oxomethyl]tetrahydropyran (2.17 g, 81%) as a white powder which was used without further purification.
Step 4. 4-[(3-((1,2- dihydro-1-methyl-2-oxoquinolin-6-yl)methoxy)-5-fluorophen-1-yl)oxomethyl]tetrahydropyran.

The desired compound was prepared according to the method of Example 1, step 5, except substituting 1,2-dihydro-1-methyl-2-oxoquinolin-6-yl-methyl bromide, prepared as described in EPA 385-679, for 2-bromomethylnaphthalene, substituting 4-[(3-hydroxy-5-fluorophen-1-yl)oxomethyl]tetrahydropyran, prepared as in step 3, for 4-[3-(hydroxyphen-1-yl)oxomethyl]tetrahydropyran, and substituting DMF for THF.

Step 5. E- and Z-O-methyl-[(3-((1,2-dihydro-1-methyl-2-oxoquinolin-6-yl)methoxy)-5-fluorophen-1-yl)oximinomethyl]tetrahydropyran.

The desired compound was prepared according to the method of Example 7 except substituting 4-[(3-((1,2-dihydro-1-methyl-2-oxoquinolin-6-yl)methoxy)-5-fluorophen-1-yl)oxomethyl]tetrahydropyran, prepared as in step 4 for 4-[(3-(naphth-2-yl)methoxyphen-1-yl)oxomethyl]tetrahydropyran. E- and Z-O-methyl-[(3-((1,2-dihydro-1-methyl-2-oxoquinolin-6-yl)methoxy)-5-fluorophen-1-yl)oximinomethyl]tetrahydropyran was isolated as a 1:1 mixture of geometrical isomers. $^1$H NMR (300 MHz, CDCl$_3$) δ7.60–7.72 (3H, m), 7.40 (1H, d, J=9 Hz), 6.52–6.80 (4H, m), 5.03 and 4.98 (2H, 2s), 3.94–3.98 (2H, m), 3.95 (1.5H, s), 3.80 (1.5H, s), 3.73 (3H, s), 3.34–3.51 (2.5H, m), 2.64 (0.5H, br pentet, J=8 Hz), 1.89 (1H, dq, J=4.5, 13, 13, 13 Hz), 1.60–1.72 (3H, m). MS 425 (M+H)$^+$, 442 (M+NH$_4$)$^+$. Analysis calc'd for C$_{24}$H$_{25}$FN$_2$O$_4$(0.25 H$_2$O): C, 67.20; H, 5.99; N, 6.53. Found: C, 67.30; H, 5.68; N, 6.23.

EXAMPLE 16

Preparation of E- and Z-4-[(3-((1,2-dihydro-1-methyl-2-oxoquinolin-6-yl)methoxy)-5-fluorophen-1-yl) oximinomethyl]tetrahydropyran.

The desired compound was prepared according to the method of Example 8, except substituting 4-[(3-((1,2-dihydro-1-methyl-2-oxoquinolin-6-yl)methoxy)-5-fluorophen-1-yl)oxomethyl]tetrahydropyran, prepared as in Example 15, steps 1–4, for 4-[(3-(naphth-2-yl)methoxyphen-1-yl)oxomethyl]tetrahydropyran. E- and Z-4-[(3-((1,2-dihydro-1-methyl-2-oxoquinolin-6-yl)methoxy)-5-fluorophen-1 -yl)oximinomethyl]tetrahydropyran was isolated as a 2:3 mixture of E:Z isomers. $^1$H NMR (300 MHz, acetone-D$_6$) δ7.86 (1H, d, J=9.5 Hz), 7.82 (1H, d, J=1 Hz), 7.74 (1H, dd, J=9, 2 Hz), 7.56 (1H, d, J=9 Hz), 6.68–6.90 (3H, m), 6.61 (1H, d, J=9.5 Hz), 5.28 and 5.24 (0.7H and 1.3H, 2s), 3.82–3.92 (2H, m), 3.68 (3H, s), 3.29–3.50 (3H, m), 1.50–1.70 (4H, m). MS 411 (M+H)$^+$, 428 (M+NH$_4$)$^+$. Analysis calc'd for C$_{23}$H$_{23}$FN$_2$O$_4$: C, 67.31; H, 5.64; N, 6.82. Found: C, 66.96; H, 5.64; N, 6.64.

EXAMPLE 17

Preparation of E- and Z-O-methyl-3-methyl-3-[(3-((naphth-2-yl)methoxy)-5-fluorophen-1-yl)oximinomethyl]oxetane.

Step 1. 3-methyloxetane-3-carboxaldehyde.

Pyridinium chlorochromate (31.6 g, 147 mmol) was added to a mixture of 3-methyl-3-oxetanemethanol (10 g, 97.9 mmol) and molecular seives (97.9 g) in CH$_2$Cl$_2$. The reaction mixture was stirred for 45 min at ambient temperature. The dark-brown suspension was filtered through a pad of florasil and the filtrate was concentrated in vacuo. 3-methyloxetane-3-carboxaldehyde (4.11 g) was isolated by chromatography on silica gel (ethyl acetate).
Step 2. 3-methyl-3-[(3-benzyloxy-5-fluorophen-1-yl)hydroxymethyl]oxetane.

The desired compound was prepared according to the method of Example 1, step 3 except substituting 3-benzyloxy-5-fluorobromobenzene for 3-methoxymethoxy-bromobenzene, and substituting 3-methyloxetane-3-carboxaldehyde for tetrahydro-4H-pyran-4-(N,O-dimethyl)carboxamide.

Step 3. 3-methyl-3-[(3-benzyloxy-5-fluorophen-1-yl)oxomethyl]oxetane.

To a solution of 3-methyl-3-[(3-benzyloxy-5-fluorophen-1-yl)hydroxymethyl]oxetane (1.85 g, 6.1 mmol) in acetone (27 mL) was added a solution of $K_2Cr_2O_7$ (1.64 g), and concentrated $H_2SO_4$ (1.2 mL) in $H_2O$ (10 mL). The reaction mixture was stirred for 3.5 hours at ambient temperature and was then partitioned between ethyl acetate and $H_2O$. The aqueous phase was extracted three times with ethyl acetate. The combined organic layers were neutralized with saturated aqueous $HaHCO_3$, washed with brine, and concentrated in vacuo to provide 3-methyl-3-[(3-benzyloxy-5-fluorophen-1-yl)oxomethyl]oxetane (1.9 g) as a yellow oil which was used without further purification.

Step 4. 3-methyl-3-[(3-hydroxy-5-fluorophen-1-yl)oxomethyl]oxetane.

The desired compound was prepared according to the method of Example 15, step 3, except substituting 3-methyl-3-[(3-benzyloxy-5-fluorophen-1-yl)oxomethyl]oxetane, prepared as in step 3, for 4-[(3-benzyloxy-5-fluorophen-1-yl)oxomethyl]-tetrahydropyran.

Step 5. 3-methyl-3-[(3-((naphth-2-yl)methoxy)-5-fluorophen-1-yl)oxomethyl]oxetane.

The desired compound was prepared according to the method of Example 1, step 5 except substituting 3-methyl-3-[(3-hydroxy-5-fluorophen-1-yl)oxomethyl]oxetane, prepared as in step 4, for 4-[3-(hydroxyphen-1-yl)oxomethyl]tetrahydropyran.

Step 6. E- and Z-O-methyl-3-methyl-3-[(3-((naphth-2-yl)methoxy)-5-fluorophen-1-yl)oximinomethyl]oxetane.

The desired compound was prepared according to the method of Example 7 except substituting 3-methyl-3-[(3 -((naphth-2-yl)methoxy)-5-fluorophen-1 -yl)oxomethyl]oxetane, prepared as in step 5, for 4-[(3-(naphth-2-yl)methoxyphen-1-yl)oxomethyl]tetrahydropyran. E- and Z-O-Methyl-3-methyl-3-[(3-((naphth-2-yl)methoxy)-5-fluorophen-1-yl)oximinomethyl]oxetane was isolated as a 2:1 mixture of E:Z isomers. $^1$H NMR (300 MHz, acetone-$D_6$) $\delta$8.01 (1H, br s), 7.89–7.98 (3H, m), 7.63 (1H, dt, J=9, 2, 2 Hz), 7.50–7.57 (2H, m), 6.93 and 6.91 (1H, 2 dt, J=10.5, 3, 3 Hz), 6.81 and 6.70 (1H, 2br t, J=1.5 Hz), 6.75 and 6.59 (1H, 2 ddd, J=9, 2, 1 Hz), 5.38 and 5.36 (2H, 2 s), 4.99 and 4.63 (2H, d, J=6 Hz), 4.28 and 4.22 (2H, d, J=6 Hz), 3.92 and 3.77 (3H, 2 s), 1.82 and 1.52 (3H, 2 s). MS 380 (M+H)+, 397 (M+NH$_4$)+. Analysis calc'd for $C_{23}H_{22}FNO_3$: C, 72.81; H, 5.84; N, 3.69. Found: C, 72.55; H, 5.55; N, 3.53.

EXAMPLE 18

Preparation of E- and Z-3-methyl-3-[(3-((naphth-2-yl)methoxy)-5-fluorophen-1-yl)oximinomethyl]oxetane.

The desired compound was prepared according to the method of Example 8, except substituting 3-methyl-3-[(3-((naphth-2-yl)methoxy)-5-fluorophen-1 -yl)oxomethyl]oxetane, prepared as in Example 17, steps 1–5, for 4-[(3-(naphth-2-yl)methoxyphen-1-yl)oxomethyl]-tetrahydropyran. E- and Z-3-methyl-3-[(3-((naphth-2-yl)methoxy)-5-fluorophen-1-yl)-oximinomethyl]oxetane was isolated as a 1:1 mixture of E:Z isomers. $^1$H NMR (300 MHz, CDCl$_3$) $\delta$7.83–7.91 (4H, m), 7.48–7.55 (3H, m), 7.13 (1H, br t, J=1 Hz), 6.62–7.03 (2H, 4 sets of overlapping m), 5.24 and 5.22 (2H, 2 s), 4.70 (4H/2, A$\overline{B}$, J=8 Hz), 4.37 (4H/2, A$\overline{B}$, J=8 Hz), 4.39 (2H/2, $\overline{AB}$, J=8 Hz), 4.18 (2H/2, A$\overline{B}$, J=8 Hz), 3.82 (2H/2, $\overline{AB}$, J=11.5 Hz), 3.68 (2H/2, $\overline{AB}$, J=11.5 Hz), 1.88 and 1.37 (3H, 2 s). MS 366 (M+$\overline{H}$)+, 383 (M+NH$_4$)+.

Analysis calc'd for $C_{22}H_2O$ $FNO_3$(0.25 $H_2O$): C, 71.43; H, 5.51; N, 3.78. Found: C, 71.50; H, 5.39; N, 3.68.

EXAMPLE 19

Preparation of E- and Z-3-[(3-((naphth-2-yl)methoxy)-5-fluorophen-1-yl)oximinomethyl]oxetane.

Step 1.3-[(3-((naphth-2-yl)methoxy)-5-fluorophen-1-yl)oxomethyl]oxetane.

The desired compound is prepared according to the method of Example 17, steps 1–5, except substituting 3-oxetanemethanol for 3-methyloxetane-3-methanol.

Step 2. E- and Z-3-[(3-((naphth-2-yl)methoxy)-5-fluorophen-1-yl)oximinomethyl]oxetane.

The desired compound is prepared according to the method of Example 18, except substituting 3-[(3-((naphth-2-yl)methoxy)-5-fluorophen-1-yl)oxomethyl]oxetane, prepared as in step 1, for 4-[(3-(naphth-2-yl)methoxyphen-1yl)oxomethyl]tetrahydropyran.

EXAMPLE 20

Preparation of E- and Z-O-methyl-[(3-((naphth-2-yl)methoxy)-5-fluorophen-1-yl)oximinomethyl]oxetane.

The desired compound is prepared according to the method of Example 7 except substituting 3-[(3-((naphth-2-yl)methoxy)-5-fluorophen-1-yl)oxomethyl]oxetane, prepared as in Example 19, step 1, for 4-[(3-(naphth-2-yl)methoxyphen-1-yl)oxomethyl]tetrahydropyran.

EXAMPLE 21

Preparation of E- and Z-3-[(3-((1,2-dihydro-1-methyl-2-oxoquinolin-6-yl)methoxy)-5-fluorophen-1- yl)oximinomethyl]oxetane.

Step 1. 3-[3-((1,2-dihydro-1-methyl-2-oxoquinolin-6-yl)methoxy)-5-fluorophen-1-yl)oxomethyl]oxetane.

The desired compound is prepared according to the method of Example 17, steps 1–5 except substituting 3-oxetanemethanol for 3-methyl-3-oxetanemethanol, and substituting 1,2-dihydro-1-methyl-2-oxoquinolin-6-yl-methyl bromide, prepared as described in EPA 385–679, for 2-bromomethylnaphthalene.

Step 2. E- and Z-3-[(3-((1,2-dihydro-1-methyl2-oxoquinolin-6-yl)methoxy)-5-fluorophen-1-yl)oximinomethyl]oxetane.

The desired compound is prepared according to the method of Example 18, except substituting 3-[(3-((1,2-dihydro-1-methyl-2-oxoquinolin-6-yl)methoxy)-5-fluorophen-1-yl)oxomethyl]oxetane, prepared as in step 1, for 4-[(3-(naphth-2-ylmethoxyphen-1-yl)oxomethyl]tetrahydropyran.

EXAMPLE 22

Preparation of E- and Z-O-methyl-3-[(3-((1,2-dihydro-1-methyl-2-oxoquinolin-6-yl)methoxy)-5-fluorophen-1-yl)oximinomethyl]oxetane.

The desired compound is prepared according to the method of Example 7 except substituting 3-[(3-((1,2-dihydro-1-methyl-2-oxoquinolin-6-yl)methoxy)-5-fluorophen-1-yl)oxomethyl]oxetane, prepared as in Example 21, step 1, for 4-[(3-(naphth-2-yl)methoxyphen-1-yl)oxomethyl]tetrahydropyran.

EXAMPLE 23

Preparation of E and
Z-4-[(3-((naphth-2-yl)thioxy)phen-1-yl)oximinomethyl]tetrahydropyran.

Step 1. 4-[((3-thioxy)phen-1-yl)oxomethyl]tetrahydropyran.

The desired compound is prepared according to the method of Example 1, step 3, except substituting 3-bromothiophenol for 3-methoxylmethoxybromobenzene and using 2 equivalents of n-BuLi.

Step 2. 4-[(3-((naphth-2-yl)thioxy)phen-1-yl)oxomethyl]tetrahydropyran.

The desired compound is prepared by reaction of 2-iodonaphthalene and 4-[((3-thioxy)phen-1-yl)oxomethyl]tetrahydropyran, prepared as in step 1, in the presence of copper(I) chloride.

Step 3. E and Z-4-[(3-((naphth-2-yl)thioxy)phen-1-yl)oximinomethyl]tetrahydropyran.

The desired compound was prepared according to the method of Example 8, except substituting 4-[(3-((naphth -2-yl)thioxy)phen-1-yl)oxomethyl]tetrahydropyran, prepared as in step 2, for 4-[(3-(naphth-2-yl)methoxyphen-1yl)oxomethyl]tetrahydropyran.

EXAMPLE 24

Preparation of E and
Z-O-methyl-4-[(3-((naphth-2-yl)thioxy)phen-1-yl)oximinomethyl]tetrahydropyran.

The desired compound is prepared according to the method of Example 7 except substituting 4-[(3-((naphth-2-yl)thioxy)phen-1-yl)oxomethyl]tetrahydropyran, prepared as in Example 23, step 2, for 4-[(3-(naphth-2-yl)methoxyphen-1-yl)oxomethyl]tetrahydropyran.

EXAMPLE 25

Preparation of E- and
Z-4-[(3-((1,2-dihydro-1-methyl-2-oxoquinolin-6-yl)thioxy)phen-1-yl)oximinomethyl]tetrahydropyran.

Step 1. 4-[(3-((1,2-dihydro-1-methyl-2-oxoquinolin-6-yl)thioxy)phen-1-yl)oxomethyl]tetrahydropyran.

The desired compound is prepared according to the method of Example 23, step 2, except substituting 6-iodo-3-1,2-dihydro-1-methyl-2-oxoquinolin, prepared as described in EPA 420 511, for 2-iodonaphthalene.

Step 2. E- and Z-4-[(3-((1,2-dihydro-1-methyl2-oxoquinolin-6-yl)thioxy)phen-1-yl)oximinomethyl]tetrahydropyran.

The desired compound was prepared according to the method of Example 8, except substituting 4-[(3-((1,2-dihydro-1-methyl-2-oxoquinolin-6-yl)thioxy)-5-fluorophen-1-yl)oxomethyl]tetrahydropyran, prepared as in step 1, for 4-[(3-(naphth-2-yl)methoxyphen-1-yl) oxomethyl]tetrahydropyran.

EXAMPLE 26

Preparation of E- and
Z-O-methyl-4-[(3-((1,2-dihydro-1-methyl2-oxoquinolin-6-yl)thioxy)phen-1-yl)oximinomethyl]tetrahydropyran.

The desired compound is prepared according to the method of Example 7 except substituting 4-[(3-((1,2-dihydro-1-methyl-2-oxoquinolin-6-yl)thioxy)-5-fluorophen-1-yl)oxomethyl]tetrahydropyran, prepared as in Example 25, step 1, for 4-[(3-(naphth-2-yl)methoxyphen-1-yl)oxomethyl]tetrahydropyran.

EXAMPLE 27

Preparation of E- and
Z-4-[(3-((naphth-2-yl)thioxy)-5-fluorophen-1-yl)oximinomethyl]tetrahydropyran.

Step 1. 3-thiophenoxy-5-fluorobromobenzene.

The desired compound was prepared according to the method of Example 15, step 1, except substituting thiophenol for benzyl alcohol.

Step 2. 3-thioxy-5-fluoro-bromobenzene.

The desired compound is prepared by treatment of 3-thiophenoxy-5-fluoro-bromobenzene with trifluoroacetic acid and phenol at 30° C. for two hours.

Step 3. E- and Z-4-[(3-((naphth-2-yl)thioxy)-5-fluorophen-1-yl)oximinomethyl]tetrahydropyran.

The desired compound is prepared according to the method of Example 23, except substituting 3-thioxy-5-fluoro-bromobenzene for 3-bromothiophenol.

EXAMPLE 28

Preparation of E- and
Z-O-methyl-4-[(3-((naphth-2-yl)thioxy)-5-fluorophen-1-yl)oximinomethyl]tetrahydropyran.

The desired compound is prepared according to the method of Example 7 except substituting 4-[(3-9(naphth-2-yl)thioxy)-5-fluorophen-1-yl)oxomethyl]tetrahydropyran, prepared as in Example 27, for 4-[(3-(naphth-2-ylmethoxy)phen-1-yl)oxomethyl]tetrahydropyran.

EXAMPLE 29

Preparation of E- and
Z-4-[(3-((1,2-dihydro-1-methyl-2-oxoquinolin-6-yl)thioxy)-5-fluorophen-1-yl)oximinomethyl]tetrahydropyran.

The desired compound is prepared according to the method of Example 25, except substituting3-thioxy-5-fluoro-bromobenzene, prepared as in Example 27, steps 1 and 2, for 3-bromothiophenol.

EXAMPLE 30

Preparation of E- and Z-O
methyl-4-[(3-((1,2-dihydro-1-methyl2-oxoquinolin-6-yl)thioxy)-5-fluorophen-1-yl)oximinomethyl]tetrahydropyran The desired compound is prepared according to the method of Example 7 except substituting 4-[(3-((1,2-dihydro-1-methyl-2-oxoquinolin-6-yl)thioxy)-5-fluorophen-1-yl)oxomethyl]tetrahydropyran, prepared as in Example 29, for 4-[(3-(naphth-2-yl)methoxyphen-1-yl)oxomethyl]tetrahydropyran.

EXAMPLE 31

Preparation of
4-[(3-((naphth-2-yl)thioxy)phen-1-yl)methoxymethyl]-tetrahydropyran.

Step 1. 4-[(3-((naphth-2-yl)thioxy)phen-1-yl)hydroxymethyl]tetrahydropyran.

The desired compound is prepared according to the method of Example 1, step 6, except substituting 4-[(3-((naphth-2-yl)thioxy)phen-1-yl)oxomethyl]tetrahydropyran, prepared as in Example 23, step 2, for 4[(3-(naphth-2-ylmethoxyphen-1-yl)oxomethyl]tetrahydropyran.

Step 2. 4-[(3-((naphth-2-yl)thioxy)phen-1-yl)methoxymethyl]tetrahydropyran.

The desired compound is prepared according to the method of Example 2, except substituting 4-[(3-((naphth-2-yl)thioxy)phen-1-yl)hydroxymethyl]tetrahydropyran, prepared as in step 1, for [(3-(naphth-2-yl)methoxyphen-1-yl)hydroxymethyl]tetrahydropyran.

EXAMPLE 32

Preparation of 4-[(3-((1,2-dihydro-1-methyl-2-oxoquinolin-6-yl)thioxy)phen-1-yl)methoxymethyl]tetrahydropyran.

The desired compound is prepared according to the method of Example 31, except substituting 4-[(3-((1,2-dihydro-1-methyl-2-oxoquinolin-6-yl)thioxy)phen-1-yl)oxomethyl]tetrahydropyran, prepared as in Example 25, step 1, for 4-[(3-((naphth-2-yl)thioxy)phen-1-yl)oxomethyl]tetrahydropyran.

EXAMPLE 33

Preparation of 4-[(3-((naphth-2-yl)thioxy)-5-fluorophen-1-yl)methoxymethyl]tetrahydropyran.

The desired compound is prepared according to the method of Example 31, except substituting 4-[(3-((naphth-2-yl)thioxy)-5-fluorophen-1-yl)oxomethyl]tetrahydropyran, prepared as in Example 27, for 4[(3-(naphth-2-yl)methoxyphen-1-yl)oxomethyl]tetrahydropyran.

EXAMPLE 34

Preparation of 4-[(3-((1,2-dihydro-1-methyl-2-oxoquinolin-6-yl)thioxy)-5-fluorophen-1-yl)methoxymethyl]tetrahydropyran.

The desired compound is prepared according to the method of Example 31, except substituting 4-[(3-((1,2-dihydro-1-methyl-2-oxoquinolin-6-yl)thioxy)-5-fluorophen-1-yl)oxomethyl]tetrahydropyran, prepared as in Example 25, step 1, for 4-[(3-((naphth-2-yl)thioxy)phen-1-yl)oxomethyl]tetrahydropyran.

The compounds represented in Table 2 are prepared by alkylation of appropriate alcohol, obtained as described in Examples 1 (X=H), or 15 (X=F) with the requisite 3-heteroaryl-prop-2-yn-yl halide which was prepared as described in the patent literature (EP-385-663, Crawley, G. C.), followed by conversion to the desired oxime as described in Examples 7 (R=Me), or 8 (R=H).

TABLE 2

Novel Aryl- and Heteroarylacetylene Substituted Oxime Ethers

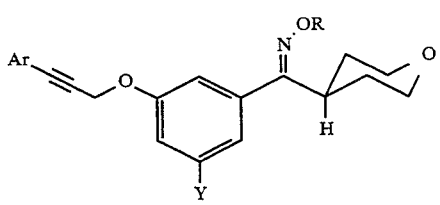

| Example | R | Y | Ar |
|---|---|---|---|
| 35 | H | H | -2-pyridyl |
| 36 | Me | F | -2-pyridyl |
| 37 | Me | H | -3-pyridyl |
| 38 | H | F | -3-pyridyl |
| 39 | H | H | -4-pyridyl |
| 40 | Me | F | -4-pyridyl |
| 41 | Me | H | -2-furyl |
| 42 | H | F | -2-furyl |
| 43 | H | H | -3-furyl |
| 44 | Me | F | -3-furyl |
| 45 | H | H | -2-thienyl |
| 46 | Me | F | -2-thienyl |

TABLE 2-continued

Novel Aryl- and Heteroarylacetylene Substituted Oxime Ethers

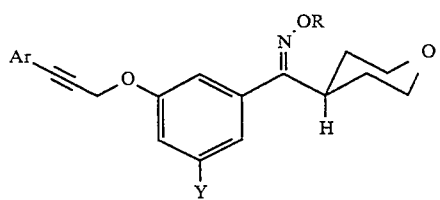

| Example | R | Y | Ar |
|---|---|---|---|
| 47 | Me | H | -3-thienyl |
| 48 | H | F | -3-thienyl |
| 49 | H | H | -2-benzo[b]thienyl |
| 50 | Me | F | -2-benzo[b]thienyl |
| 51 | Me | H | -2-benzo[b]furyl |
| 52 | H | F | -2-benzo[b]furyl |
| 53 | H | H | -2-thiazolyl |
| 54 | Me | F | -2-thiazolyl |
| 55 | Me | H | -2-imidazolyl |
| 56 | H | F | -2-imidazolyl |
| 57 | H | H | -2-pyrimidyl |
| 58 | Me | F | -2-pyrimidyl |

The compounds represented in Table 3 are prepared by alkylation of appropriate alcohol, obtained as described in Examples 1 (X=H), or 15 (X=F) with the requisite 3-heteroaryl-prop-2-yn-yl halide which was prepared as described in the patent literature (EP-385-663, Crawley, G. C.), followed by reduction of the ketone and alkylation of the resulting alcohol as described in Examples 1 and 2.

TABLE 3

Novel Aryl- and Heteroarylacetylene Substituted Methine Ethers

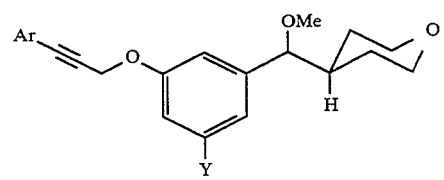

| Example | Y | Ar |
|---|---|---|
| 59 | H | -2-pyridyl |
| 60 | F | -2-pyridyl |
| 61 | H | -3-pyridyl |
| 62 | F | -3-pyridyl |
| 63 | H | -4-pyridyl |
| 64 | F | -4-pyridyl |
| 65 | H | -2-furyl |
| 66 | F | -2-furyl |
| 67 | H | -3-furyl |
| 68 | F | -3-furyl |
| 69 | H | -2-thienyl |
| 70 | F | -2-thienyl |
| 71 | H | -3-thienyl |
| 72 | F | -3-thienyl |
| 73 | H | -2-benzo[b]thienyl |
| 74 | F | -2-benzo[b]thienyl |
| 75 | H | -2-benzo[b]furyl |
| 76 | F | -2-benzo[b]furyl |
| 77 | H | -2-thiazolyl |
| 78 | F | -2-thiazolyl |
| 79 | H | -2-imidazolyl |
| 80 | F | -2-imidazolyl |
| 81 | H | -2-pyrimidyl |
| 82 | F | -2-pyrimidyl |

The compounds represented in Table 4 are prepared according to the method of Example 1, except substituting the requisite arylmethyl halide for 2-bromomethylnaphthalene followed by conversion to the desired oxime as described in Examples 7 (R=Me), or 8 (R=H).

TABLE 4
Novel Aryl- and Heteroarylmethyloxy Substituted Oxime Ethers

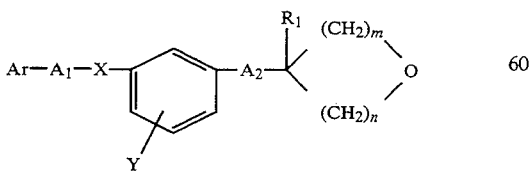

| Example | R | Ar |
|---------|---|-----|
| 83 | H | -quinoxalin-6-yl |
| 84 | Me | -quinoxalin-6-yl |
| 85 | H | -quinolin-6-yl |
| 86 | Me | -quinolin-6-yl |
| 87 | H | 1-methyl-2-oxo-1,2,3,4-tetrahydroquinolin-6-yl |
| 88 | Me | 1-methyl-2-oxo-1,2,3,4-tetrahydroquinolin-6-yl |
| 89 | H | 2,2,4-trimethyl-3-oxo-2,3-dihydro-4H-1,4-benzoxazin-7-yl |
| 90 | Me | 2,2,4-trimethyl-3-oxo-2,3-dihydro-4H-1,4-benzoxazin-7-yl |
| 91 | H | 1,3-dimethyl-2-oxo-2,3-dihydrobenz-imidazol-5-yl |
| 92 | Me | 1,3-dimethyl-2-oxo-2,3-dihydrobenz-imidazol-5-yl |

The compounds represented in Table 5 are prepared according to the method of Example 2, except substituting the desired ketone for 4-[3-((naphth-2-yl)methoxyphen-1-yl)oxomethyl]tetrahydropyran.

TABLE 5
Novel Substituted Aryl- and Heteroaryl- Methine Ethers

| Example | Ar |
|---------|-----|
| 93 | -quinoxalin-6-yl |
| 94 | -quinolin-6-yl |
| 95 | 1,2-dihydro-N-methyl-2-oxo-quinolin-6-yl |
| 96 | 1-methyl-2-oxo-1,2,3,4-tetrahydroquinolin-6-yl |
| 97 | 2,2,4-trimethyl-3-oxo-2,3-dihydro-4H-1,4-benzoxazin-7-yl |
| 98 | 1,3-dimethyl-2-oxo-2,3-dihydrobenz-imidazol-5-yl |

We claim:

1. A compound having the structure

Ar—A₁—X—[aryl with Y]—A₂—C(R₁)((CH₂)ₘ-O-(CH₂)ₙ)

or a pharmaceutically acceptable salt thereof wherein
Ar is selected from the group consisting of
(a)

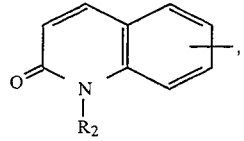

(b)

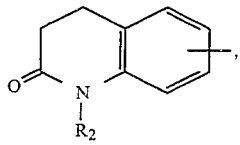

(c)

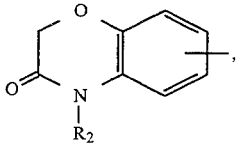

and
(d)

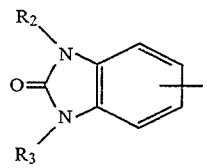

wherein R₂ and R₃ are independently hydrogen or alkyl of from one to four carbon atoms;
A₁ is a valence bond or is propynylene or methylene;
X is selected from the group consisting of O, S, SO₂, or NR₂, where R₂ is as defined above;
Y is selected from the group consisting of
hydrogen,
alkyl of from one to six carbon atoms,
haloalkyl of from one to six carbon atoms,
alkoxy of from one to six carbon atoms, and
halogen;
A₂ is selected from the group consisting of
(a)

wherein R₄ is selected from the group consisting of
hydrogen,
alkyl of from one to four carbon atoms,
alkenyl of from three to six carbon atoms,
alkynyl of from three to six carbon atoms, and
alkoxyalkyl in which the alkoxy and alkyl groups can independently contain from one to four carbon atoms;
(b)

wherein Z is selected from the group consisting of $OR_5$ and $NR_5$, where $R_5$ is selected from the group consisting of hydrogen and alkyl of from one to four carbon atoms; and (c) methylene;

$R_1$ is selected from the group consisting of hydrogen, alkyl of from one to four carbon atoms, and $OR_5$ where $R_5$ is as defined above;

m is 1 or 2; and n is 1 or 2.

2. A compound as defined in claim 1 or a pharmaceutically acceptable salt thereof wherein $A_2$ is

where $R_3$ is defined therein.

3. A compound as defined in claim 1, or a pharmaceutically acceptable salt thereof wherein $A_2$ is

where Z is $OR^5$ where $R^5$ is as defined therein.

4. A compound as defined in claim 1, or a pharmaceutically acceptable salt thereof wherein $A_2$ is methylene.

5. A compound or pharmaceutically acceptable salt thereof selected from the group consisting of 4-((3-((1,2-dihydro-1-methyl-2-oxoquinolin-6-yl)methoxy)phen-1yl)methoxymethyl)tetrahydropyran;

4-((3-((1,2-dihydro-1-methyl-2-oxoquinolin-6-yl) methoxy)phen-1-yl)methoxymethoxymethyl)tetrahydropyran;

E- and Z-4-((3-((1,2-dihydro-1-methyl-2-oxoquinolin-6-yl)methoxy)phen-1-yl)oximinomethyl)tetrahydropyran;

E- and Z-O-methyl-4-((3-((1,2-dihydro-1-methyl-2-oxoquinolin-6-yl)methoxy)phen-1-yl)oximinomethyl)tetrahydropyran;

E- and Z-O-ethyl-4-((3-((1,2-dihydro-1-methyl-2-oxoquinolin-6-yl)methoxy)phen-1-yl)oximinomethyl)tetrahydropyran;

E- and Z-O-methyl-((3-((1,2-dihydro-1-methyl-2-oxoquinolin-6-yl)methoxy)-5-fluorophen-1-yl)oximinomethyl)tetrahydropyran; and E- and Z-4-((3-((1,2-dihydro-1-methyl-2-oxoquinolin-6-yl)methoxy)-5-fluorophen-1-yl)oximinomethyl)-tetrahydropyran.

6. A pharmaceutical composition for inhibiting 5-lipoxygenase enzyme activity comprising a therapeutically effective amount of a compound as defined by claim 1 in combination with a pharmaceutically acceptable carrier.

7. A method of inhibiting 5-lipoxygenase enzyme activity comprising administering to a mammal in need of such treatment a therapeutically effective amount of a compound as defined by claim 1.

* * * * *